US006350272B1

(12) United States Patent
Kawesch

(10) Patent No.: US 6,350,272 B1
(45) Date of Patent: Feb. 26, 2002

(54) METHOD AND APPARATUS FOR CUTTING AN OBLONG CORNEAL FLAP

(76) Inventor: Glenn Kawesch, P.O. Box 675584, Rancho Santa Fe, CA (US) 92067-5584

( * ) Notice: Subject to any disclaimer, the term of this patent is extended or adjusted under 35 U.S.C. 154(b) by 0 days.

(21) Appl. No.: 09/532,849

(22) Filed: Mar. 20, 2000

(51) Int. Cl.[7] .................................................. A61F 9/00
(52) U.S. Cl. ............................... 606/166; 606/5; 606/4
(58) Field of Search ................................ 606/4–6, 107, 606/166, 167, 169

(56) References Cited

U.S. PATENT DOCUMENTS

| 4,766,895 A | * | 8/1988 | Reynolds .................... 128/303 |
| 4,840,175 A | | 6/1989 | Peyman .................... 128/303.1 |
| 4,903,695 A | | 2/1990 | Warner et al. ................. 606/4 |
| 5,133,726 A | | 7/1992 | Ruiz et al. ................... 606/166 |
| 5,423,841 A | * | 6/1995 | Kornefeld ................... 606/166 |
| 5,533,997 A | | 7/1996 | Ruiz .............................. 606/5 |
| 5,586,980 A | * | 12/1996 | Kremer et al. ................. 606/4 |
| 5,658,303 A | | 8/1997 | Koepnick ................... 606/166 |
| 5,817,115 A | * | 10/1998 | Nigam ........................ 606/166 |
| 5,964,776 A | | 10/1999 | Peyman ...................... 606/166 |
| 5,984,916 A | * | 11/1999 | Lai ............................... 606/11 |
| 6,007,553 A | | 12/1999 | Hellenkamp et al. ....... 606/166 |
| 6,019,754 A | | 2/2000 | Kawesch ....................... 606/4 |
| 6,030,398 A | * | 2/2000 | Klopotek .................... 606/166 |
| 6,099,541 A | * | 8/2000 | Klopotek .................... 606/166 |
| 6,197,038 B1 | * | 3/2001 | O'Donnell, Jr. ............ 606/166 |

* cited by examiner

Primary Examiner—Michael Peffley
Assistant Examiner—Peter J Vrettakos
(74) Attorney, Agent, or Firm—Borque & Associates, P.A.

(57) ABSTRACT

An apparatus and method is used to cut a substantially oblong corneal flap to facilitate reshaping of a live cornea. In particular, the method and apparatus of cutting a substantially oblong corneal flap is used during laser in situ keratomileusis (LASIK) surgery to correct hyperopia. A cornea holding device is positioned over the live cornea such that a portion of the cornea extends through a substantially oblong opening in the cornea holding device. The portion of the cornea conforms to the oblong shape of the opening and is cut to form a substantially oblong corneal flap. The substantially oblong corneal flap is folded over to expose an oblong inner corneal surface. A laser is directed at the oblong corneal surface to ablate a ring-shaped region. The oblong shape of the corneal flap and the exposed inner corneal surface allows the laser ablation to occur without damaging the connecting portion of the corneal flap or corneal blood vessels which extend vertically in the cornea. When the corneal flap is repositioned, the laser ablation in the ring-shaped region changes the shape of the cornea in a way that will increase curvature of the cornea and correct hyperopia.

11 Claims, 2 Drawing Sheets

METHOD AND APPARATUS FOR CUTTING AN OBLONG CORNEAL FLAP

FIELD OF THE INVENTION

The present invention relates to ophthalmologic surgery and more particularly, relates to a method and apparatus for cutting an oblong corneal flap to facilitate laser in situ keratomileusis (LASIK) surgery to correct hyperopia.

BACKGROUND OF THE INVENTION

A normal ametropic eye includes a cornea, lens and retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia (near sightedness), hypermetropia or hyperopia (far sightedness), and astigmatism.

A myopic eye has either an axial length that is longer than that of a normal eye, or a cornea or lens having a refractive power stronger than that of the cornea and lens of a normal eye. This stronger refractive power causes the far points to be projected in front of the retina. Conversely, a hypermetropic or hyperopic eye has either an axial lens shorter than that of a normal eye, or a lens or cornea having a refractive power less than that of a lens and cornea of a normal eye. This lesser refractive power causes the far point to be focused on the back of the retina. An eye suffering from astigmatism has a defect in the lens or shape of the cornea and is incapable of sharply focusing images on the retina.

Various approaches have been taken to correct such disorders by properly focusing light onto the retina. Glasses can be used to correct such disorders but are sometimes considered awkward and inconvenient, particularly for individuals with an active lifestyle. Although contact lenses have addressed some of the inconveniences of glasses, contact lenses present additional problems with care and maintenance and possibly irritation or damage to the eye.

More recently, different types of surgery have been used to change the shape of the cornea and correct eye disorders. Examples of such surgical procedures include automated lamellar keratectomy (ALK) and laser in situ keratomileusis (LASIK). According to both of these procedures, a thin layer of the cornea is cut using a microsurgical instrument known as a microkeratome. Removing the thin layer of cornea allows the live cornea to be reshaped in a way that corrects the disorder. Examples of microkeratomes are disclosed in U.S. Pat. No. 5,133,726 to Ruiz et al., U.S. Pat. No. 5,964,776 to Peyman, and U.S. Pat. No. 6,007,553 to Hellenkamp et al., all of which are incorporated herein by reference.

The use of the LASIK procedure to correct hyperopia presents a unique problem. As shown in FIG. 1, the cornea 12 of an eye 10 is cut to form a corneal flap 16. The corneal flap 16 is folded over at a connecting portion 18 to expose the freshly cut, inner corneal surface 20. To affect correction of hyperopia, laser light 2 is directed at an ring-shaped region 22 on the inner corneal surface 20, as shown in FIG. 2. When the corneal flap 16 is repositioned and reattached, the ablation of the cornea 12 in this ring-shaped region 22 increases the curvature of the cornea and corrects the hyperopia.

One problem encountered with this procedure is the need for a large treatment area 22 which begins to approach the vertical regions of the cornea which contain blood vessels 19. If a sufficiently large circular corneal flap 16 is cut, there is a significant risk of corneal bleeding due to cutting of the blood vessels 19. An additional problem adds to the risk of severing a blood vessel which is that the connecting portion 18 of the corneal flap may interfere with the treatment region 22. Therefore, there is a tension between making the corneal flap large enough to accommodate the treatment region 22 while not cutting corneal blood vessels 19.

Accordingly, there is a need for a method and apparatus for cutting the corneal flap in a way that allows the cornea to be shaped without interfering with the connecting portion of the flap and without significant risk of severing or cutting blood vessels.

SUMMARY OF THE INVENTION

The present invention features a method of performing LASIK surgery to correct hyperopia. The method comprises the steps of positioning a cornea holding device over a live cornea to stabilize the live cornea such that a portion of the live cornea extends through an oblong opening in the cornea holding device. An oblong corneal flap is then cut from the live cornea extending through the oblong opening in the cornea holding device and is folded over to expose a freshly cut, inner corneal surface. A laser is then directed at a ring-shaped region on the inner corneal surface to ablate the inner corneal surface at the ring-shaped region. The oblong corneal flap is then repositioned onto the inner corneal surface to allow the oblong corneal flap to reattach. The oblong shape of the corneal flap allows the ring-shaped region to be ablated without interfering with the connecting portion of the corneal flap.

The present invention also features a method of cutting an oblong corneal flap to facilitate reshaping of a live cornea. The method comprises the steps of positioning a cornea holding device over a live cornea to stabilize the live cornea such that a portion of the live cornea extends through an oblong opening in the corneal holding apparatus. A cutting tool is then moved across the portion of the live cornea to separate the portion of the live cornea, while leaving a connecting portion of the live cornea intact to form the oblong corneal flap.

The present invention also features an apparatus for cutting an oblong corneal flap comprising a cornea holding device having an oblong opening for receiving an oblong portion of a live cornea. A cutting tool is positioned above the cornea holding device for cutting the oblong portion of the live cornea to form the oblong corneal flap.

DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENT

Figure 1:
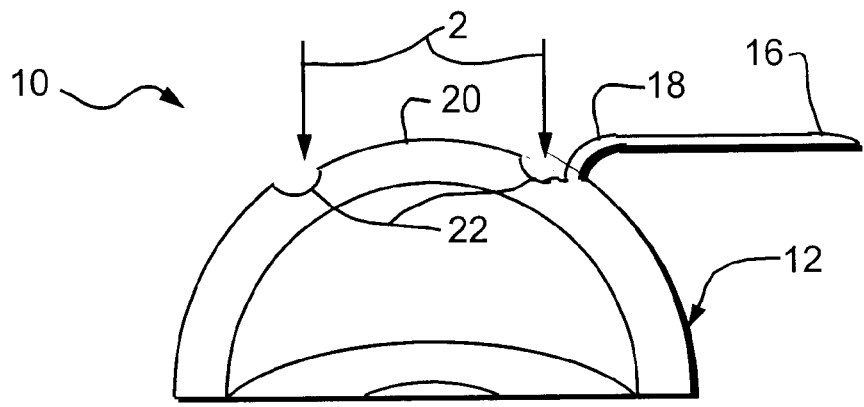
FIG. 1 is a side view of an eye with a resected corneal flap, according to the prior art technique.
Figure 2:
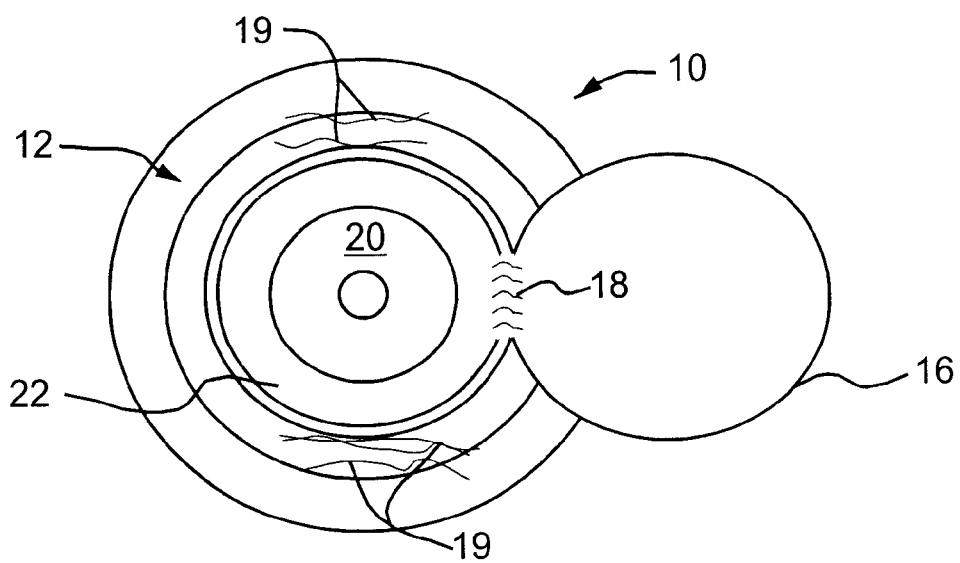
FIG. 2 is a top view of the eye having the resected corneal flap cut according to the prior art technique.
Figure 3:
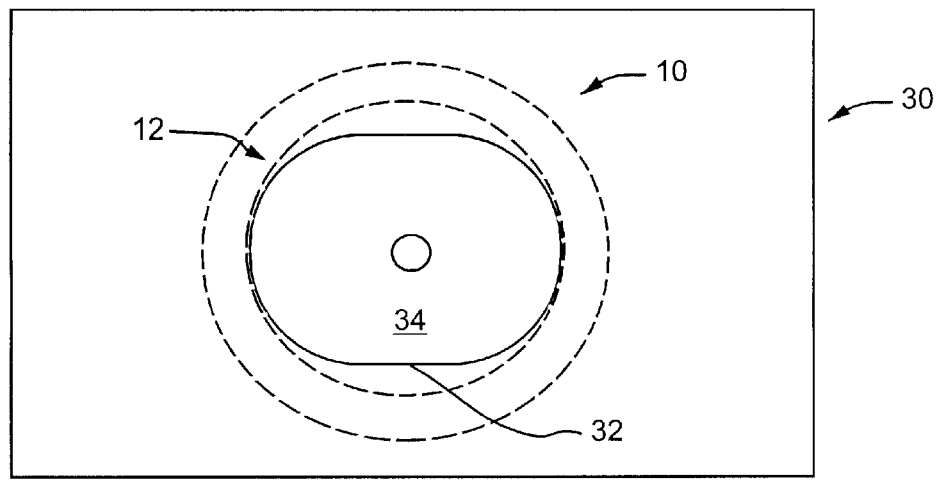
FIG. 3 is a top view of a cornea holding device positioned over an eye, according to the present invention.

The apparatus, according to the present invention, includes a cornea holding device 30, FIG. 3, having an oblong opening 32. The cornea holding device 30 is positioned over the eye 10, using techniques known to those of ordinary skill in the art. An oblong shaped portion 34 of the cornea 12 is positioned to extend through the oblong opening 32 by methods well known in the art, such as by applying suction. Although the oblong opening 32 and corresponding oblong portion 34 of the cornea 12 are shown as having a substantially oval shape, as used herein, oblong or substantially oblong shape shall mean any oblong, oval or similar shape that is longer horizontally than vertically.

Figure 4:
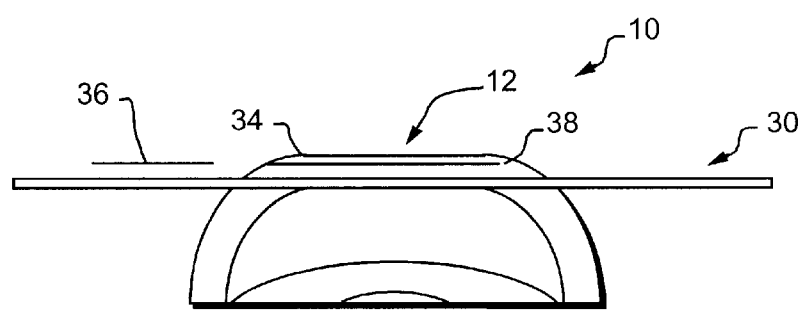
FIG. 4 is a side view of a cornea holding device positioned over the eye, according to the present invention.
Figure 5:
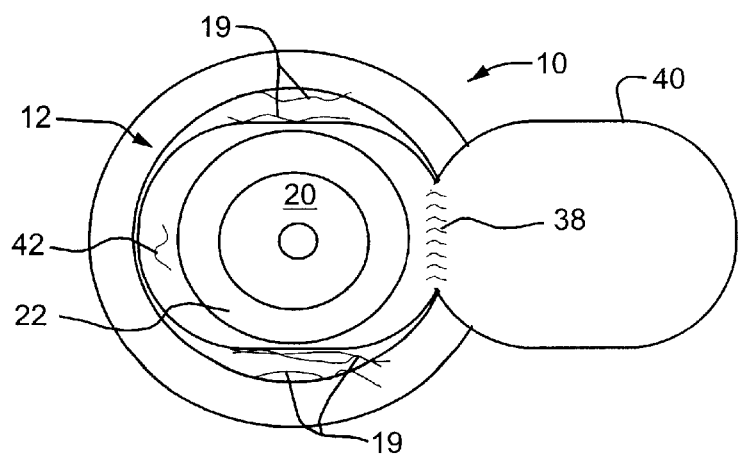
FIG. 5 is a top view of an eye having an oblong corneal flap cut according to the present invention.

The apparatus of the present invention also includes a cutting tool 36, FIG. 4. When the cornea 12 is stabilized by the cornea holding device 30, the cutting tool 40 is used to cut the substantially oblong portion 34 of the cornea 12, using techniques known to one of ordinary skill in the art. The oblong portion 34 of the cornea 12 is cut leaving intact a connecting portion 38 of the cornea 12, thereby forming an oblong corneal flap 40, as shown in FIG. 5.

The concept of cutting an oblong corneal flap of the present invention can be implemented using any type of microkeratome or other cornea cutting device. The devices disclosed in U.S. Pat. Nos. 5,133,726; 5,964,776; and 6,007,553 all use some type of cornea holding device (also referred to as a retaining ring assembly or positioning ring) having a circular opening through which the cornea is forced to extend. The teachings of these patents are fully incorporated herein by reference. According to the present invention, the cornea holding device in these prior art devices is modified such that the opening has a substantially oblong shape.

When the oblong corneal flap 40 is folded over, a freshly cut, inner corneal surface 42 having a substantially oblong shape is exposed which has an oblong shape extending in the horizontal direction corresponding to that of the oblong corneal flap 40. To correct hyperopia, a laser (not shown) is then used to ablate the ring-shaped region 22 on the inner corneal surface 42. The oblong shape of the corneal flap 40 and inner corneal surface 42 thus allows the ring-shaped region 22 to be ablated without interfering with the connecting portion 38 and without cutting blood vessels 19 found generally in the vertical direction.

Examples of using laser ablation for correcting hyperopia are disclosed in U.S. Pat. No. 4,840,175 to Peyman and U.S. Pat. No. 4,903,695 to Warner et al., both of which are incorporated herein by reference. Other techniques for reshaping an inner cornea surface exposed beneath a corneal flap can also be used.

When the cornea has been properly reshaped, the corneal flap 40 is repositioned and allowed to adhere to the inner corneal surface 42. In one embodiment, the present invention can be used together with the METHOD AND APPARATUS FOR IMPROVING LASIK FLAP ADHERENCE, disclosed in U.S. Pat. No. 6,019,754 issued to the inventor of the present invention and fully incorporated herein by reference. According to this method, compressed air is applied to the corneal flap repositioned on the cornea to dry the corneal flap and facilitate adherence. The ablation in the ring-shaped region 22 increases the curvature of the cornea 12 when the corneal flap 40 adheres, thereby correcting the hyperopia.

Accordingly, the method and apparatus of the present invention cuts an oblong shaped corneal flap and allows for the correction of hyperopia by laser ablation without interfering with or damaging the connecting tissue on the corneal flap.

Modifications and substitutions by one of ordinary skill in the art are considered to be within the scope of the present invention which is not to be limited except by the claims which follow.

What is claimed is:

1. An apparatus for cutting a substantially oblong corneal flap, comprising:
    a cornea holding device having a substantially oblong opening for receiving a substantially oblong portion of a live cornea; and
    a cutting tool, positioned above said cornea holding device, for cutting said substantially oblong portion of said live cornea to form said substantially oblong corneal flap.

2. The apparatus of claim 1 wherein said substantially oblong opening has a first dimension in the horizontal direction which is greater than a second dimension in the vertical direction.

3. The apparatus of claim 1 further including apparatus for applying compressed air to said substantially oblong corneal flap repositioned onto said inner corneal surface to dry said corneal flap.

4. The apparatus of claim 1 wherein said apparatus includes a microkeratome.

5. A method of performing laser in situ keratomileusis (LASIK) surgery to correct hyperopia, said method comprising the steps of:
    positioning a cornea holding device over a live cornea to stabilize said live cornea, wherein a portion of said live cornea extends through a substantially oblong opening in said cornea holding device;
    cutting a substantially oblong corneal flap from said live cornea extending through said substantially oblong opening in said cornea holding device;
    folding said substantially oblong corneal flap over to expose a freshly cut, inner corneal surface;
    directing a laser at a region on said inner corneal surface to ablate at least one region of said inner corneal surface; and
    re-positioning said substantially oblong corneal flap onto said inner corneal surface to allow said substantially oblong corneal flap to reattach.

6. The method of claim 5 further including the step of applying compressed air to said substantially oblong corneal flap repositioned onto said inner corneal surface to dry said corneal flap.

7. The method of claim 5 wherein cutting step is performed using a microkeratome.

8. The method of claim 5 wherein said substantially oblong corneal flap has a first dimension in the horizontal direction which is greater than a second dimension in the vertical direction.

9. A method of cutting an oblong corneal flap to facilitate re-shaping of a live cornea, said method comprising the steps of:
    positioning a cornea holding device over a live cornea to stabilize said live cornea, wherein a portion of said live cornea extends through a substantially oblong opening in said cornea holding device;
    moving a cutting tool across said portion of said live cornea to separate said portion of said cornea; and
    leaving a connecting portion of said live cornea intact to form said substantially oblong corneal flap.

10. The method of claim 5 wherein said substantially oblong corneal flap has a first dimension in the horizontal direction which is greater than a second dimension in the vertical direction.

11. The method of claim 5 further including the step of applying compressed air to said substantially oblong corneal flap repositioned onto said inner corneal surface to dry said corneal flap.

* * * * *